United States Patent [19]
Godfroid et al.

[11] Patent Number: 5,817,460
[45] Date of Patent: Oct. 6, 1998

[54] NUCLEIC ACID PROBES SPECIFIC TO THE SPIROCHETE *BORRELIA BURGDORFERI*

[75] Inventors: Edmond Godfroid, Brussels; Alex Bollen, Itterbeek, both of Belgium

[73] Assignee: La Region Wallonne, Brussels, Belgium

[21] Appl. No.: 513,764

[22] PCT Filed: Feb. 18, 1994

[86] PCT No.: PCT/BE94/00012

§ 371 Date: Aug. 21, 1995

§ 102(e) Date: Aug. 21, 1995

[87] PCT Pub. No.: WO94/19488

PCT Pub. Date: Sep. 1, 1994

[30] Foreign Application Priority Data

Feb. 19, 1993 [BE] Belgium ............................. 09300161

[51] Int. Cl.⁶ ............................ C07H 21/04; C12Q 1/68; C12P 19/34
[52] U.S. Cl. ............................ 435/6; 435/912; 435/810; 536/23.1; 536/24.32; 536/24.33; 935/8; 935/78
[58] Field of Search ............................ 435/6, 91.2, 810; 536/24.32, 24.33, 23.1; 935/8, 78

[56] References Cited

U.S. PATENT DOCUMENTS 5,571,718  11/1996  Dunn ................................... 435/252.3

FOREIGN PATENT DOCUMENTS

| WO 9004411 | 5/1990 | WIPO . |
| WO 9209703 | 6/1992 | WIPO . |
| WO 9300448 | 1/1993 | WIPO . |
| WO 9304175 | 3/1993 | WIPO . |
| WO 9308306 | 4/1993 | WIPO . |

OTHER PUBLICATIONS

Caporale et al (Jan. 1994) Molecular Biology Evolution 11(1): 51–64.

Barbour et al, *Microbiological Reviews,* 50(4):381–400 (1986).

Szczepanski et al, *Microbiological Reviews,* 55(1):21–34 (1991).

Lonneux et al, *Revue Des Questions Scientifiques,* 2:190–208 (1990).

Saiki et al, *Science,* 230:1350–1354.

Marconi et al, *J. Bacteriol.,* 174(1):241–244 (1992).

Baranton et al, *Int. J. Syst. Bacteriol.,* 42(3):378–383 (1992).

Hassen et al, *J. Clin. Microbiol.,* 26(2):338–346 (1988).

Feng et al, *J. Mol. Evol.,* 25:351–360 (1987).

Lefebvre et al, *J. Clin. Microbiol.,* 28(4):700–706 (1990).

Simpson et al, *Infect. Immun.,* 58(4):847–853 (1990).

Fellinger et al, *Gene,* 120:127–128 (1992).

Wilske et al, *J. Clin. Microbiol.,* 31(2):340–350 (1993).

Assous et al, *V. International Conference on Lyme Borreliosis,* Article 06, p. 243 (1992).

*Primary Examiner*—Carla J. Myers
*Attorney, Agent, or Firm*—Sughrue, Mion, Zinn, Macpeak & Seas, PLLC

[57] ABSTRACT

The invention relates to an oligonucleotide agent suited to use in evidencing at least one strain of *Borrelia burgdorferi.*

Proposed are sequences common to all the groups of *Borrelia burgdorferi* strains, suited to use either as primers during genetic amplification reactions, or as capture probes in a hybridization test on a solid support on which the target DNA is "sandwiched" between the said capture probe and a disclosure probe, or else as disclosure probes in the said hybridization test on a solid support.

Also proposed are sequences specific to each of the groups of Bb strains, suited to use as primers during genetic amplification reactions or as disclosure or capture probes in the hybridization test on the solid support mentioned above.

34 Claims, No Drawings

NUCLEIC ACID PROBES SPECIFIC TO THE SPIROCHETE *BORRELIA BURGDORFERI*

This invention relates to an oligonucleotide agent which can be used to evidence at least one strain of *Borrelia burgdorferi*, and to the varied applications of the said oligonucleotide agent.

The spirochete *Borrelia burgdorferi* (Bb) is the causative agent of Lyme disease. The vector host of this spirochete is an acarid of the genus Ixodes, *I. ricinus* in Europe or *I. dammini* and *I. pacificus* in North America. Clinical diagnosis of the illness relies on various anatomical and pathological signs (erythema chronicum migrans (ECM), fever, arthritis, meningitis and in the most severe cases myocarditis) [1]. The search for anti-OspA antibody (glycoprotein situated at the Bb surface) and/or anti-flagelline antibody (flagellum protein) constitutes the chief method of immuno-biochemical diagnosis of this illness [2]. This search for anti-Borrelia antibodies does, however, entail a number of drawbacks. It is dependent on the reactivity of the host's immune system vis-à-vis Bb, which determines the sensitivity of this type of detection system. This immuno-biochemical method also has the drawback of not being able to dissociate a possible reaction that overlaps with infectious agents closely related to Bb (for example Treponema pallidum, which is responsible for syphilis) from a specific recognition [3]. It would therefore be helpful to develop new diagnostic tools that overcome these difficulties. The detection of the DNA of Bb using molecular hybridization techniques that employ a nucleotide probe and a target DNA fulfils these conditions. These hybridization experiments are generally carried out on a solid support (a nitrocellulose or nylon filter) to which the target DNA is attached, or alternatively in a liquid medium, for example at the time of a genetic amplification reaction known as the "Polymerase Chain Reaction", or PCR, which requires the presence of the target DNA, two nucleotide probes or primers specific to the target DNA, and a polymerization enzyme known as Taq polymerase [4]. These molecular hybridization techniques are highly sensitive (capable of detecting a single bacterial genome) and highly specific. They have the advantage that they do not depend on any physiological or pathological reaction whatsoever of the infected host organism.

Thanks to molecular hybridization studies on the entire Bb genome it is now possible to separate a large number of known strains into three major groups [6]. This breakdown into different groups is likewise evidenced by comparing the sequence of the gene coding for the OspA surface glycoprotein of different strains of Bb using a customized computer program. The results of this computer analysis are corroborated by a phylogenetic study carried out on the gene coding for 16S ribosomal RNA [5]. Analysis of this classification of Bb strains in relation to the clinical signs observed in the course of the illness suggests a useful link between a strain's membership of a particular group and the pathology associated therewith; for example, the strains subsumed under group I show a tendency to induce arthritic signs, whilst those belonging to group II principally cause neuroboreliosis [7].

The detection of a Bb infection is currently done by using the serum of the potentially infected patient to recognize the purified flagellar antigen fixed on an Elisa type plate. This recognition is evidenced by the addition of an anti-human antibody associated with a disclosure enzyme or a molecule employing this type of enzyme [8].

Within the area of epidemiological studies, the routine diagnosis of infections by different known groups of Bb and the follow-up of the efficacy and composition of vaccines affording protection against Bb infections, it is helpful to develop simple, specific and sensitive techniques based on the use either of synthetic DNA probes labelled non-isotopically and suited to use in molecular hybridization reactions on a solid support, or synthetic DNA primers suited to use in genetic amplification reactions (PCR). With this aim in mind, we have used computer processing to identify, within the sequence of the gene coding for the OspA surface glycoprotein of Bb, regions capable of being used as probes or primers in molecular hybridization reactions.

It is an object of the present invention to propose sequences common to all of the groups of Bb strains, which can be used either as primers in the course of genetic amplification reactions (PCR), or as a capture probe in a hybridization test on a solid support where the target DNA is "sandwiched" between the said capture probe and a disclosure probe, or else as disclosure probes in-this hybridization test on a solid support.

It is a further object of this invention to propose specific sequences of each of the groups of Bb strains, which can be used as primers in the course of genetic amplification reactions (PCR) or as disclosure or capture probes in the hybridization test on the solid support mentioned above.

These various objects are achieved by the use of an oligonucleotide agent as defined in the main claim.

Among the sequences defined in the main claim, those of particular interest are the sequences common to all the groups of *Borrelia burgdorferi* strains and group-specific sequences.

1. Sequences common to all groups of *Borrelia burgdorferi* strains

A. Suited to use in genetic amplification reactions (PCR)

One object of the present invention is therefore nucleic acid primers that can be used for the genetic amplification of the DNA of all the groups of known Bb strains. Comparing the sequence of the gene coding for OspA surface glycoprotein, using a customized computer program, allows this type of primer to be targeted.

The PCR reaction requires the use of two nucleic acid primers. One is situated on the coding strand; the other is situated on the complementary strand downstream of the first primer. Table 1 below sets out the sequence of two pairs of primers enabling the amplification of a fragment of DNA inside the sequence of the OspA gene of all the groups of Bb strains. This table also sets out the position of these primers on the known sequence of the OspA gene of strain B31, their semi-hybridization temperature and their respective size.

A, T, C, G represent the nucleotides corresponding to the bases adenine, thymine, cytosine and guanine, respectively.

TABLE 1

| Probes | Sequences | Length | Tm | Position |
| --- | --- | --- | --- | --- |
| OspApc1 | AATAGGTCTA ATATTAGCCT TAATAGC (SEQ ID NO:1) | 27 | 70° C. | 21–47 |
| OspApc2 | CTAGTGTTTT GCCATCTTCT TTGAAAA (SEQ ID NO:2) | 27 | 70° C. | 328–302 |

The sequences in this table are presented in the orientation 5'→3'. The sequence of the OspApc2 primer is presented in inverse complementary mode to the sequence of the coding strand (or of the direct fiber).

The use of the OspApc1/OspApc2 primers in a PCR reaction generates a DNA fragment having 282 base pairs (bp).

pc signifies "conserved primers".

B. Suited to capturing DNA originating from all the groups of *Borrelia burgdorferi* strains A further object of the present invention is a sequence common to all the groups of Bb strains that are suited to use in "capturing" DNA originating from all these groups in a so-called sandwich test, in which oligonucleotide probes specific to each of the groups or common to all the groups of Bb strains are used to disclose the Bb DNA "capture" probe molecular hybrid. Such a "capture" probe may be attached by a covalent bond to a suitable support. Under such a system, the target DNA is sandwiched between the capture oligonucleotide and the disclosure probe.

It has been possible to define the sequence of this capture oligonucleotide common to all the groups of Bb strains through computer comparison of the sequences of the gene coding for the OspA surface glycoprotein. The sequence of this oligonucleotide is as follows:

Bb50:5'-ATGAAAAAAT ATTTATTGGG AATAGGTCTA ATATTAGCCT TAATAGCATG-3'(SEQ ID NO:3)

The sequence of this oligomer comprises 50 nucleotides; it is situated on the coding strand of the OspA gene and extends from position 1 to 50 of the coding sequence of the OspA gene of strain B31.

C. Suited to disclosing a hybridization reaction between the capture probe and the target DNA Another object of the present invention is probes that can be used to identify the Bb genus as opposed to other bacteria. These oligonucleotide probes common to all the groups of Bb strains make it possible to disclose the presence of a molecular hybrid constituted by the capture probe and the target DNA, in a hybridization test as described above under section 1.B.

These disclosure probes are chemically modified by the addition at 5' and/or at 3' of one or more molecular grouping (s) having an affinity for a molecule associated with an enzyme, for example alkaline phosphatase. This enzyme is able to react either with a colourless, soluble, chromogenic substrate which gives a coloured reaction product or a chemiluminescent substrate, for example AMPPD™ or CSPD™ (Tropix, USA).

These disclosure probes comprise a nucleic acid sequence as follows:

for the oligomer Bb35bio:
    5'-GCAACAGTAG ACAAGCTTGA GCTTAAAGGA ACTTC-3'(SEQ ID NO:4)

for the oligomer Bb23bio:
    5'-TTTTCAAAGA AGATGGCAAA ACA-3'(SEQ ID NO:5)

The oligomers Bb35bio and Bb23bio, which are common to all groups of Bb strains, have 35 and 23 monomers respectively. Their sequence extends respectively from position 166 to 200 and from position 302 to 324 of the coding sequence of the OspA gene of strain B31.

2. Group-specific sequences

A. Suited to use in genetic amplification reaction (PCR)

A further object of the present invention is specific primers of each of the groups of Bb strains suited to use in a PCR reaction. The type I primers, annotated as BbGI1 and BbGI2, permit amplification of a DNA fragment characteristic of the strains of this group. The primers of groups II, symbolized by BbGII1 and BbGII2, permit amplification of a DNA fragment characteristic of group II, whereas the group III primers, symbolized by BbGIII1, BbGIII2 and BbGIII3, when combined pairwise, for example BbGIII1 and BbGIII2, permit amplification of a DNA fragment characteristic of group III strains.

The sequence of these group-specific primers, presented from the 5' extremity to the 3' extremity, is as follows:

for the group I strains, the primers:
    BbGI1: 5'-AACAAAGACG GCAAGTACGA TCTAATT-3'(SEQ ID NO:6) BbGI2: 5'-TTACAGTAAT TGTTAAAGTT GAAGTGCC-3' (SEQ ID NO:7)

for the group II strains, the primers:
    BbGII1: 5'-TGATAAAAAC AACGGTTCTG GAAC-3'(SEQ ID NO:8)
    BbGII2: 5'-GTAACTTTCA ATGTTGTTTT GCCG-3' (SEQ ID NO:9)

for the group III strains, the primers:
    BbGIII1: 5'-GAAAAAGGTG AATTGTCTGC AAAAACC-3'(SEQ ID NO:10)
    BbGIII2: 5'-TTCCAATGTT ACTTTATCAT TAGCTACTT-3'(SEQ ID NO:11)
    BbGIII3: 5'-TAAAGACAAA ACATCAACAG ATGAAATG'3'(SEQ ID NO:12)

The oligomers BbGI1 and BbGI2 begin respectively at position 139 and 682 on the coding sequence of the OspA gene of strain B31 (a group I strain). These oligomers are respectively constituted by 27 and 28 nucleotides. Their semi-hybridization temperature is 74° C. Oligomer BbGI2 is presented in inverse complementary mode to the coding strand. The use of these two oligomers in a PCR reaction permits the amplification of a DNA fragment of 544 base pairs (bp).

The oligomers BbGII1 and BbGII2 begin respectively at position 201 and 545 on the coding sequence of the OspA gene of strain B29 (a group II strain). These oligomers are both constituted by 24 nucleotides. Their semi-hybridization temperature is 66° C. Oligomer BbGII2 is presented in inverse complementary mode to the coding strand. The use of these two oligomers in a PCR reaction permits the amplification of a DNA fragment of 345 base pairs (bp).

The oligomers BbGIII1, BbGIII2 and BbGIII3 begin respectively at position 381, 536 and 347 on the coding sequence of the OspA gene of strain Aca1 (a group III strain). These oligomers are constituted respectively by 27, 29 and 28 nucleotides. The semi-hybridization temperature is 74° C. for oligomers BbGIII1 and BbGIII2, and 72° C. for oligomer BbGIII3. Oligomer BbGII2 is presented in inverse complementary mode to the coding strand. The use of oligomers BbGIII1 and BbGIII2 in a PCR reaction permits the amplification of a DNA fragment of 155 base pairs (bp). Following amplification, the BbGIII3/BbGIII2 oligomer pair generates a DNA fragment of 188 bp.

B. Suited to use in direct or indirect detection, at the time of a DNA/DNA hybridization reaction, of different groups of *Borrelia burgdorferi* strains Another object of the present invention is nucleic acid probes specific to each of the groups of Bb strains suited to use in direct or indirect detection of the different groups of Bb strains. Direct detection may be carried out by hybridization of the target DNA affixed to a solid support, for example nitrocellulose or nylon, by one of these probes belonging to one of the known groups of Bb strains. Indirect detection may be carried out via the "sandwich" system of molecular hybridization outlined in section 1.B. In this case, the capture probe may be either a probe common to all the groups of Bb strains or a probe specific to each of the groups. Such "capture" probes may likewise be attached by a covalent bond to a suitable support. In this so-called sandwich test, the disclosure oligonucleotides will be either the Bb35bio or Bb23bio oligomer when the capture probe is specific to each of the Bb groups, or the BbGI23, BbGII123 or BbGIII28 oligomer when the capture probe is common to all the Bb groups. These probes are associated with a molecule having an affinity for a molecule associated with an enzyme, for example alkaline phosphatase. In the same way, in a system of direct detection the probes are modified as outlined above.

The sequence of these oligomers, presented in the 5'-3' direction, is as follows:

for the group I BbGI23 oligomer:
5'-CTGCAGCTTG GAATTCAGGC ACT-3'(SEQ ID NO:13)

for the group II BbGII23 oligomer:
5'-ACTCTAGCTG CTGACGGCAA AAC-3'(SEQ ID NO:14)

for the group III BbGIII28 oligomer:
5'-AGGAAAAGTA GCTAATGATA AAGTAACA-3' (SEQ ID NO:15)

The BbGI23 oligomer starts at position 638 and ends at position 660 of the coding sequence of the OspA gene of strain B31 (a group I strain). It is constituted by 23 nucleotides. Its semi-hybridization temperature is 70° C.

Oligomer BbGII23 starts at position 508 and ends at position 530 of the coding sequence of the OspA gene of strain B29 (a group II strain). It is constituted by 23 nucleotides. Its semi-hybridization temperature is 70° C.

The BbGIII128 oligomer starts at-position 503 and ends at position 530 of the coding sequence of the OspA gene of strain Aca1 (a group III strain). It is constituted by 28 nucleotides. Its semi-hybridization temperature is 70° C.

There now follow some examples of applications for the oligonucleotide agents described herein.

A. Diagnosis of *Borrelia burgdorferi* (Bb) in body fluids of infected subjects

The Bb spirochete infects the host animal following a bite from an infected tick (*Ixodes ricinus* in Europe). At the site of the bite there rapidly develops (in a few hours) an annnular erythema and then erythema chronicum migrans (ECM). The spirochete then invades various organs and tissues of the host (bladder, central nervous system, cartilage tissue) after being transported by the blood and the liver. It is therefore helpful to use an appropriate system of detection (PCR with original primers specific to Bb or "sandwich" hybridization test with original nucleotide probes specific to Bb) to analyze the body fluids that may potentially be infected with Bb following a bite by a tick. The blood and urine are fluids of choice in view of the ease with which samples are taken. When articular signs (arthritis) or neurologic signs appear, it is helpful to use these original systems of molecular investigation on the synovial and cephalo-rachidian fluids.

B. Human and veterinary applications

The use of our detection system, based on probes and/or molecular primers specific to Bb, on human specimens is demonstrated in section 3.A. outlined above. This detection system may be extended to specimens of animal origin. Cats, dogs, bovidae and equidae may be host animals to Bb. Lameness in horses may be due to Bb infection of the joint between the tibia and the tarsal bone. Some authors have demonstrated the presence of Bb in cow's milk. It is therefore helpful to apply our proposed system of detection to specimens of veterinary origin that would potentially be infected with Bb.

C. Aid to the treatment of infection

Studies on molecular hybridization between the entire Bb genome have made it possible to separate a large number of known strains into 3 major groups. Computer comparison of the known sequence of the OspA gene of several Bb strains has likewise evidenced the breakdown of these different Bb strains into 3 major groups. The analysis of this classification of the Bb strains in relation to the clinical signs observed over the course of the disease shows a useful link between a strain's membership of a given group and the pathology associated therewith; for example, the strains subsumed in group I show a tendency to cause arthritic signs whereas those belonging to group II mainly cause neuroboreliosis. The group III strains, for-their part, essentially give rise to acrodermatitis.

The relationship between membership of a group and a specific pathology developed during more advanced stages of the illness is an important factor for the clinician. The clinician will adapt his medication (type of antibiotic, dosage, treatment duration) in response to the various results which he will have amassed when analyzing the symptoms and biochemically investigating the various samples of body fluids taken. Speedy, specific and reliable detection of the Bb group infecting the patient at early stages of the illness will provide the clinician with a precise indication as to the type of evolution he can expect if the medicine does not have the desired effects. This diagnostic response will enable the clinician to adapt his treatment in order to prevent the illness from progressing to more worrying stages from the clinical viewpoint (neurologic and cardiac impairment, chronic stage of the disease) The use of our detection system, based on original probes and/or molecular primers, specific to each of the groups of Bb strains, makes it possible to achieve this objective.

D. Epidemiology and investigation of reservoir animals

An epidemiological study of Lyme disease covers two aspects: the first comprises a study of the vector of the disease, *Ixodes ricinus*; the other comprises the analysis of reservoir animals (wild and domestic). The vector of this disease is a mite (*Ixodes ricinus*) which develops in undergrowth with a high humidity content in three stages: larva, nymph and adult. At each phase of development, *Ixodes ricinus* takes a meal of blood in the course of which it may become infected if it comes into contact with an animal contaminated with Bb. The host wild animal par excellence of Bb is the roe deer, by virtue of the superposition of the roe deer biotope onto that of the tick. Nonetheless, the host wild animals that are potential reservoirs of the disease are very diverse. They may be rodents (field mice, hares, rabbits, etc.), birds (blackbirds, sparrows, etc.), suidae (wild boar), cervidae. (roe deer, fallow deer, red deer) or alternatively canidae (wolves and foxes).

An epidemiological study of the Bb vector and of the wild animals listed above will make it possible not only to identify the geographical areas at high risk of infection, but also to measure the extent of infection in the three stages of development of the vector and of the wild animals that are potential reservoirs of the spirochete. The detection method as proposed by us, based on molecular hybridization between the target DNA and a probe or an original primer pair specific to Bb, enables this type of objective to be achieved.

E. Follow-up of the efficacy of vaccination

The vaccination of patients living in geographical regions with high Bb endemicity, or patients whose activities (gamekeepers, foresters, farmers, walkers) bring them into these regions, constitutes the prophylactic method enabling the painful and debilitating clinical signs associated with Lyme disease to be avoided. Nevertheless, a certain number of patients may escape the protection targeted by the vaccine. It is therefore helpful to follow up the efficacy of the proposed vaccines by detecting Bb in vaccinated patients presenting with clinical signs associated with Lyme disease. The detection method as proposed by us, based on molecular hybridization between the target DNA and a probe, or an original primer pair specific to Bb, enables this type of objective to be achieved.

F. Follow-up of vaccine composition

The effectiveness of a vaccine is determined by its protective power vis-à-vis the target pathogenic agent. In the specific case of Bb, the vaccine may be developed by attempting to build up immunity against OspA surface glycoprotein. A good knowledge of the sequence of this gene taken from a large number of different strains belonging to different groups helps in the structuring of a vaccine of this type. A certain number of authors have noted variability of the OspA gene. The reason for this variability is not yet known.

The variability of the general genetic repertoire of Bb, the variability of the OspA gene sequence and the current state of knowledge of the different strains of Bb make it necessary to be extremely vigilant when it comes to constructing this type of vaccine. The analysis of a large number of different isolates using the original molecular investigation techniques which we propose makes it possible to determine the field of application of this type of vaccine. The combined use of original probes (or primer pairs) specific to each or all of the groups of Bb strains will make it possible to assign the studied isolates to one of the known groups in the present state of the art or to place it in one of the new groups created for that purpose.

The invention will now be described in more concrete terms in the examples which follow:

EXAMPLE 1

A. Determining the oligonucleotide sequences common to all *Borrelia burgdorferi* groups One of the objects of the present invention is to propose sequences common to all groups of Bb strains, suited to use either as primers in PCR reactions, or as a capture probe in a hybridization test on a solid support where the target DNA is sandwiched between said capture probe and a disclosure probe, or alternatively as disclosure probes in said "sandwich" hybridization test or in a direct detection test.

The use of sequence comparison programs ("Pileup" and "Pretty") distributed by Genetics Computer Groups, Inc. (University Research Park, 575 Science Drive, Suite B, Madison, Wis. 53711, USA) makes it possible to characterize this type of sequence. The computer program "Pileup" makes it possible to align more than 300 sequences whose length may reach 5,000 nucleotides. This program derives from a method of progressive alignment developed by Feng and Doolittle [9]. The "Pretty" program results in the alignment of the studied sequences and to the creation of a "consensus" sequence from said alignment. From this mode of presentation of the studied sequences it is possible to quickly and readily identify the target sequences common to all the groups of Bb strains that are able to act as primers in a PCR reaction, as probes in a direct or indirect detection system, or else as a capture probe in a "sandwich" type hybridization test. These nucleotide sequences possess very great homology with the target sequence.

The oligonucleotide sequences that can be used as probes common to all the groups of Bb strains are set out in Table 2 below. The sequence of these oligomers, oriented from the 5' extremity to the 3' extremity, is situated on the coding strand of the OspA gene of strain B31.

TABLE 2

| Probes | Sequences | Size | Position |
|---|---|---|---|
| Bb50 | ATGAAAAAATATTTATTGGGAATAGGTCTAATATTA GCCTTAATAGCATG (SEQ ID NO:3) | 50 | 1–50 |
| Bb35bio | GCAACAGTAGACAAGCTTGAGCTTAAAGGAACTTC (SEQ ID NO:4) | 35 | 166–200 |
| Bb23bio | TTTTCAAAGA AGATGGCAAA ACA (SEQ ID NO:5) | 23 | 302–324 |

The oligonucleotide sequences suited to use as primers common to all the groups of Bb strains, the length of these primers, their semi-hybridization temperature (Tm) and their position with respect to the coding sequence of the OspA gene of strain B31, are set out in Table 3 below. The sequence of these oligomers, oriented from the 5' extremity to the 3' extremity, is situated on the coding strand in respect of primer OspApc1; it is situated on the non-coding strand in respect of primer OspApc2. The sequence of the OspApc2 oligomer is presented in inverse complementary mode to the sequence situated on the coding strand.

TABLE 3

| Probes | Sequences | Length | Tm | Position |
|---|---|---|---|---|
| OspApc1 | AATAGGTCTA ATATTAGCCT TAATAGC (SEQ ID NO:1) | 27 | 70° C. | 21–47 |
| OspApc2 | CTAGTGTTTT GCCATCTTCT TTGAAAA (SEQ ID NO:2) | 27 | 70° C. | 328–302 |

The sequences in these probes or primers present a very high proportion of homology with the known sequences of the OspA gene of all the Bb strains. This high proportion of homology (98–100%) guarantees hybridizations or amplifications highly specific to all the Bb strains.

B. Determining DNA sequences specific to each group of *Borrelia burgdorferi* strains It is a further object of the present invention to propose nucleotide sequences specific to each group of Bb strains, suited to use either as primers in a genetic amplification reaction (PCR), or as a disclosure or capture probe in a hybridization test of the "sandwich" type, or else in a direct detection test.

The computer processing ("Pileup" and "Pretty") of the available sequences of the OspA gene of the different Bb strains makes it possible to readily identify the sequences capable of being used as a probe or primer specific to each of the known groups of Bb strains.

The oligonucleotide sequences of such probes, their position, their length and their semi-hybridization temperature are set out in Table 4 below. The position of oligomers BbGI23, BbGII23 and BbGIII28 is respectively situated on the coding strand of the OspA gene of strain B31, B29 and Aca1.

TABLE 4

| Probes | Sequences | Position | Size | Tm |
|---|---|---|---|---|
| BbGI23 | CTGCAGCTTGGAATTCAGGCACT (SEQ ID NO:13) | 638–660 | 23 | 70° C. |
| BbGII23 | ACTCTAGCTGCTGACGGCAAAAC (SEQ ID NO:14) | 508–530 | 23 | 70° C. |
| BbGIII28 | AGGAAAAGTAGCTAATGATAAAGTAACA (SEQ ID NO:15) | 503–530 | 28 | 70° C. |

The oligonucleotide sequences of the primers specific to each of the groups of Bb strains, their position, their size and their semi-hybridization temperature are set out in Table 54 below. The sequences of these primers are oriented from the 5' extremity to the 3' extremity. The position of the BbGI1 and BbGI2 oligomers refers to the coding strand of the OspA gene of strain B31 (group I); that of the BbGII1 and BbGII2 oligomers refers to the coding sequence of the OspA gene of strain B29 (group II); and, lastly, that of the BbGIII1, BbGIII2 and BbGIII3 oligomers relates to the coding sequence of the OspA gene of strain Aca1 (group III). The sequences of the BbGI2, BbGII2 and BbGIII2 oligomers are set out in inverse complementary mode to the sequence situated on the coding strand.

42° C. in the presence of the Bb23bio probe at a concentration of 50 ng per ml of hybridization solution. The Bb23bio probe was modified chemically by the addition of a molecule, for example biotin, having affinity for a molecular complex constituted by an enzymatic part, for example alkaline phosphatase.

Following hybridization, the membrane was washed successively with solutions composed either of 1% 2*SSC/SDS (0.3M sodium citrate/0.03M sodium chloride/1% sodium dodecyl sulfate); or 1% 1*SSC/SDS; or, lastly, of 1*SSC. Each wash was done at a temperature of 42° C. for 2*10 minutes.

The target DNA/probe molecular hybrids were detected by chemilumi-nescence as described in the protocol for use of the detection system "Southern-Light(, Chemiluminescent Detection System" developed by the Tropix company.

The result is that the Bb23bio probe recognizes the DNA of the 3 strains analyzed (B31, ZQ1 and Aca1). The sensi-

TABLE 5

| Primers | Sequences | Position | Size | Tm |
|---|---|---|---|---|
| BbGI1 | AACAAAGACGGCAAGTACGATCTAATT (SEQ ID NO:6) | 139–165 | 27 | 74° C. |
| BbGI2 | TTACAGTAATTGTTAAAGTTGAAGTGCC (SEQ ID NO:7) | 682–655 | 28 | 74° C. |
| BbGII1 | TGATAAAAACAACGGTTCTGGAAC (SEQ ID NO:8) | 201–224 | 24 | 66° C. |
| BbGII2 | GTAACTTTCAATGTTGTTTTGCCG (SEQ ID NO:9) | 545–522 | 24 | 66° C. |
| BbGIII1 | GAAAAAGGTGAATTGTCTGCAAAAACC (SEQ ID NO:10) | 381–407 | 27 | 74° C. |
| BbGIII2 | TTCCAATGTTACTTTATCATTAGCTACTT (SEQ ID NO:11) | 536–508 | 29 | 74° C. |
| BbGIII3 | TAAAGACAAAACATCAACAGATGAAATG (SEQ ID NO:12) | 347–374 | 28 | 72° C. |

The sequences of these group-specific probes or primers present 100% homology with the known sequences of the OspA gene of the target groups of Bb strains. This high proportion of homology guarantees hybridizations or amplifications highly specific to the different groups of Bb strains.

EXAMPLE 2

Experimental verification of the quality of the sequences common to all *Borrelia burgdorferi* groups A. Hybridization of the Bb23bio probe to the DNA of 3 strains representative of the various known groups of Bb strains The DNA of the B31 (group I), ZQ1 (group II) and Aca1 (group III) strains was prepared using the methods developed by lefebvre et al. [10] and by Simpson et al. [11]. Variable quantities (from 1 (g to 100 ng) of DNA from these 3 strains (B31, ZQ1 and Aca1) were deposited on nylon membrane (Hybond N, Amersham) using the Bio-DotR apparatus supplied by the firm BioRad. The DNAs were then affixed to the membrane by a 3-minute ultraviolet treatment (wavelength: 254 nm). The membrane was pre-hybridized and hybridized using the protocol presented by the firm Tropix (Tropix Inc., 47 Wiggins Avenue, Bedford, Mass. 01730, USA). This protocol comprises incubation of the membrane for 1 hour at a temperature of 37° C. in a hybridization solution (1 mM EDTA, 7% (w/v) SDS, 0.25M disodic phosphate, pH 7.2, 1% I-Block( ). The membrane is then hybridized in this solution overnight at a temperature of tivity of the system makes it possible to detect ±100 ng of DNA (equivalent to 100 106 copies of *Borrelia burgdorferi* DNA).

B. Genetic amplification (PCR) of DNA fragments characteristic of all the known groups of Bb strains by the OspApc1 and OspApc2 primers Another object of the present invention is oligonucleotide primers which can be used for the amplification of DNA fragments characteristic of all the Bb strains.

The OspApc1 and OspApc2 primers allow a DNA fragment of 282 base pairs characteristic of all the Bb strains to be amplified. To obtain this DNA fragment, the genetic amplification reaction is carried out on 100 ng of DNA prepared by the methods developed by lefebvre et al [9] and by Simpson et al. [10]. This PCR reaction is conducted in two phases:

a phase of denaturation of the target DNA, for 10 minutes at 96° C., an amplification phase comprising 3 steps repeated 35 times. The first step permits hybridization of the primers to the target DNA; the second step carried out at 72° C. ensures synthesis of a DNA complementary to the target DNA by the use of the polymerization enzyme, the Taq polymerase; and, lastly, the third step permits dissociation of the hybrids formed during the first two steps.

As part of the use of the OspApc1 and OspApc2 primers in this type of reaction, the hybridization step was carried out at 60° C. for 1 minute, the polymerization step was performed at 72° C. for 2 minutes, and the step of dissociating the hybrids was carried out at 94° C. for 1 minute.

The DNAs of 3 strains (B31, ZQ1 and Aca1) representative of each of the groups of Bb strains were analyzed using the PCR method indicated above. One-tenth of the PCR reaction was analyzed on Agarose gel containing 3 % Nusieve and 1% SeaKem. As a result a fragment of 282 base pairs is obtained for the 3 analyzed strains after electrophoresis, coloration of the gel with ethidium bromide, and visualization on a UV transluminator. This indicates the high quality of the OspApc1 and OspApc2 primers to be used in a PCR reaction and their potential for recognizing strains belonging to the 3 known groups of Bb strains.

EXAMPLE 3

Experimental verification of the quality of the sequences specific to each of the known groups of *Borrelia burgdorferi* strains A. Hybridization of the group-specific probes (BbGI23, BbGII23 and BbGIII8) to DNA from 3 strains representative of the different known groups of Bb strains The procedure for preparing DNA from 3 strains representative of the different known groups of Bb strains (B31 for group I, ZQ1 for group II and Aca1 for group III) and evidencing of the target DNA/probe (BbGI23 or BbGII23 or BbGIII28) molecular hybrids were carried out in conditions identical to those developed in the direct hybridization test perfected for probes common to all the known groups of Bb strains (see Example 2—section A).

Following these experimental procedures the result is that the BbGI23 probe characteristic of the group I strains specifically recognizes the DNA of strain B31 (a group I strain) at the hybridization temperature of 45°–50° C. At this hybridization temperature, the BbGI23 probe does not recognize the DNA originating from the ZQ1 strain (group II) and the Aca1 strain (group III).

As a further result, the BbGII23 probe characteristic of the group II strains specifically recognizes the DNA of strain ZQ1 (a group II strain) at the hybridization temperature of 45°–50° C. At this hybridization temperature, the BbGII23 probe does not recognize the DNA originating from the B31 strain (group I) and the Aca1 strain (group III).

Yet another result of these experimental procedures is that the BbGIII28 probe characteristic of the group III strains specifically recognizes the DNA of the Aca1 strain (a group III strain) at the hybridization temperature of 45°–50° C. At this hybridization temperature, the BbGIII28 probe does not recognize the DNA originating from the B31 (group I) and ZQ1 (group II) strains.

All these results are summarized in Table 6 below:

TABLE 6

| Probes | B31 | ZQ1 | Aca1 |
| --- | --- | --- | --- |
| BbGI23 | + | − | − |
| BbGII23 | − | + | − |
| BbGIII28 | − | − | + |

B. Genetic amplification PCR) of DNA fragments specific to each of the known groups of Bb strains A further object of the present invention is oligonucleotide primers which can be used for the amplification of DNA fragments specific to each of the known groups of Bb strains. The BbGI1 and BbGI2 primers make it possible to amplify a DNA fragment of 544 base pairs; the use of oligomers BbGII1 and BbGII2 makes it possible to amplify a DNA fragment of 345 base pairs; the BbGIII3 and BbGIII2 oligomer pair generates a DNA fragment of 188 bp after amplification. To obtain these DNA fragments, the genetic amplification reaction is carried out on 100 ng of DNA from different strains (B31, ZQ1 and Aca1) representative of the different known groups of Bb strains. The DNA of these strains is prepared by the methods described in Example 2, Section A. The PCR reaction was carried out in two phases as described in Example 2, Section B, except for the fact that the hybridization temperature for the GI1/GI2 pair was 69° C.; for the GII1/GII2 pair the said hybridization temperature was 68° C.; and, lastly, for the GIII2/GIII3 pair the hybridization temperature was 68° C.

Analysis of the products of the PCR reaction by electrophoresis gel indicates that the GI1/GI2 pair specific to the group I strains makes it possible, at a temperature of 69° C., to amplify a DNA fragment of 544 base pairs solely from DNA taken from strain B31 (group I). The use of this pair of primers in the presence of DNA taken from ZQ1 strains (group II) and Aca1 strains (group III) does not allow the amplification of this fragment of 544 base pairs.

This analysis also indicates that the GII1/GII2 pair specific to the group II strains makes it possible, at a temperature of 68° C., to amplify a DNA fragment of 345 base pairs solely from DNA originating from strain ZQ1 (a group II strain). The use of this pair of primers in the presence of DNA taken from strains B31 (group I) and Aca1 (group III) does not allow the amplification of this fragment of 345 base pairs.

A further result is that the GIII3/GII2 pair specific to the group III strains makes it possible, at a temperature of 70° C., to amplify a DNA fragment of 188 base pairs solely from DNA taken from the Aca1 strain (a group III strain). The use of this pair of primers in the presence of DNA taken from B31 strains (group I) and ZQ1 strains (group II) does not allow the amplification of this fragment of 188 base pairs.

All these results are summarized in Table 7 below:

TABLE 7

| Primers | B31 | ZQ1 | Aca1* |
| --- | --- | --- | --- |
| BbGI1/BbGI2 | + | − | − |
| BbGII1/BbGII2 | − | + | − |
| BbGIII3/BbGIII2 | − | − | + |

These results identify clearly the specificity and validity of these primers. In actual fact, the pair of primers (BbGI1/BbGI2) specific to group I only recognizes the group I strain; in the same way, the pairs of primers BbGII1/BbGII2 and BbGIII13/BbGIII2 only respectively recognize the strains belonging to group II and to group III.

EXAMPLE 4

Application of the grid to a variety of isolates of *Borrelia burgdorferi* strains Classification—Study by genetic amplification (PCR)

The molecular hybridization studies on whole Bb genome made it possible to separate a large number of known strains into 3 major groups. This breakdown into different groups is likewise evidenced by comparing the sequence of the gene coding for the OspA surface glycoprotein from different Bb strains using a customized computer program. The results of this computer analysis are corroborated by a phylogenetic study performed on the gene coding for 16S ribosomal RNA. The analysis of this classification of the Bb strains in relation to the clinical signs observed in the course of the illness suggests a useful link between the fact that a strain belongs to a given group and the pathology associated therewith; for example, the strains assigned to group I show a tendency to induce arthritic symptoms whereas those belonging to group II chiefly cause neuroboreliosis. The group III strains essentially give rise to acrodermatitis.

Various strains of Bb, whether or not classified by the molecular hybridization studies on whole genome, were analyzed by the PCR method using the group-specific primers defined in Section 2.A.—Group-specific sequences suited to use in genetic amplification reactions (PCR). The results of this analysis are elaborated in Table 8 below, where BbGI, BbGII, BbGIII and OspA respectively represent the primer pairs BbGI1 , BbGI2 (specific to group I strains), BbGII1/BbGII2 (specific to group II strains), BbGIII1 /BbGIII2 (specific to group III strains) and OspApc1/OspApc2 (characteristic of all the Bb strains).

TABLE 8

| Group | Strains | BbGI | BbGII | BbGIII | OspA |
|---|---|---|---|---|---|
| I | IP1 | ++ | − | − | + |
|  | IP2 | ++ | − | − | + |
|  | IP3 | ++ | − | − | + |
|  | 297 master | ++ | − | − | + |
|  | IRS | ++ | − | − | + |
|  | 21.038 | ++ | − | − | + |
|  | ZS7 | ++ | − | − | + |
|  | B31 | ++ | − | − | + |
| II | ZQ1 | − | ++ | − | + |
|  | Ne11H | − | + | − | + |
|  | N34 | − | + | − | + |
|  | P/Bi | − | + | − | + |
| III | Acal | − | − | ++ | + |
| IV | 20047 | − | − | − | + |
|  | G25 | + | ++ | ++ | + |
|  | VS461 | + | − | ++ | + |

As a result of this analysis it is possible to assign a large number of strains to one of the known groups of Bb strains. This classification by analyzing the PCR reaction products overlaps in part with the classification drawn up by the group headed by Baranton [6]. In actual fact, certain strains (FR47, G25 and VS461) considered by Baranton's group as being strains belonging to group II (FR47 and G25) or to group III (VS461) cannot be assigned to these groups by simple analysis of the PCR reaction products. The behaviour of these strains (FR47, G25 and VS461) vis-à-vis group-specific primers leads to the creation of a fourth group of Bb strains. The development of this type of analysis (PCR) on a larger number of isolates of Bb and the investigation of the sequence of the OspA gene of the group IV strains will make it possible to determine the validity of the classification set out in Table 8 above and may possibly also lead to the creation of new groups of Bb strains.

EXAMPLE 5

Applications to clinical specimens (human and animal) The Bb spirochete very quickly invades various target organs and tissues of the host (bladder, central nervous system, cartilage tissue) after being transported by the, blood and the liver. It is therefore helpful to use either PCR or a direct or "sandwich" type molecular hybridization system to analyze the body fluids preferentially infected with Bb.

After speedily preparing (washing, centrifugation and heat treatment) the DNA of a series of body fluids (articular liquid, cephalo-rachidian liquid, urine serum) taken from healthy subjects or subjects presenting with Lyme disease, the DNA from these samples was subjected to genetic amplification using either the group-specific primers or the primers common to all the groups of Bb strains. The results of these analyses are set out in Table 9 below:

TABLE 9

| Sample | OspA | BbGI | BbGII | BbGIII |
|---|---|---|---|---|
| LCR1 | + | ND[(1)] | ND | ND |
| LCR2 | − | ND | ND | ND |
| LCR− | − | − | − | ND |
| LAR1 | + | − | + | ND |
| LAR2 | + | − | + | ND |
| LAR3 | − | − | − | ND |
| UR1 | + | ND | ND | ND |

[(1)]ND = not determined

The results of these PCR reactions permit confirmation of the clinical diagnosis (LAR1, LAR2, UR1, LCR-) or refinement thereof (LCR1 and LCR2; negative in serology). These results make it possible to demonstrate the efficacy of the treatment administered to the patient (LAR3, LCR3 to 8). They also enable us to indicate the type of Bb strains infecting patients (LAR1 and LAR2; group II).

In the foregoing description it should be understood that the scope of the present invention likewise extends to inverse complementary sequences of probes Bb50, Bb35bio, Bb23bio, BbGI23, BbGII23 and BbGIII28.

LITERATURE REFERENCES

[1] Barbour, A. G., and S. F. Hayes. 1986. Microbiol. Rev. 50, 381–400.
[2] Szczepanski, A., and J. L. Benach. 1991. Microbiol. Rev. 55, 21–34.
[3] Lonneux, J. F., Van Impe, G., Lebrun, Ph., Tricot, J. -M., et B., Losson. 1990. Rev. Quest. Scient. 161, 189–208.
[4] Saiki, R., Scharf, S., Faloona, F., Mullis, K. B., Horn, G. T., Erlich, H. A., and N., Amheim. 1985. Scient.230, 1350–1354.
[5] Marconi, R. T., and C. F., Garon. 1992. J. Clin. Micrbiol.174, 241–244.
[6] Baranton, G., Postic, D., Saint-Girons, I., Boerlin, P., Piffaretti, J. C., Assores, M., and P. A. Grimont. 1992. Int. J. Syst. Bacteriol. 42,378–383.
[7] Assous, M. V., Postic, D., Paul, G., Nevot, P., and G., Baranton. 1992. V International Conference on Lyme Borreliosis, Abstract 06.
[8] Hansen, K., Hindersson, P., and N. S., Pedersen. 1988. J. Clin. Microbiol. 26, 338–346.
[9] Feng and Doolittle. 1987. J. Mol. Evol. 35, 351–360.
[10] Lefebvre, R. B., Land, R. S., Pergn, G.-C., Brown, J. A., and R. C., Johnson. 1990. J. Clin. Microb. 28, 700–707.
[11] Simpson, W. J., Garon, C. F., and T. G., Schwan. 1990. Infec. Imm. 58,847–853.

We claim:

1. An oligonucleotide composition useful for detecting at least one strain of *Borrelia burgdorferi* (Bb) by molecular hybridization, comprising at least one oligonucleotide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:14, and SEQ ID NO:15 or an inverse complement thereof.

2. The oligonucleotide composition as claimed in claim 1, wherein said composition comprises oligonucleotides SEQ ID NO:1 and SEQ ID NO:2.

3. The oligonucleotide composition as claimed in claim 1, wherein said composition comprises an oligonucleotide selected from the group consisting of SEQ ID NO:3, SEQ ID NO:4, and SEQ ID:5, or an inverse complement thereof.

4. The oligonucleotide composition as claimed in claim 3, wherein said composition comprises oligonucleotide SEQ ID NO:3 or an inverse complement thereof.

5. The oligonucleotide composition as claimed in claim 3, wherein said composition comprises an oligonucleotide selected from the group consisting of SEQ ID NO:4 and SEQ ID NO:5, or an inverse complement thereof, wherein said oligonucleotide is labelled with a detectable marker.

6. The oligonucleotide composition as claimed in claim 1, wherein said composition comprises oligonucleotides SEQ ID NO:6 and SEQ ID NO:7.

7. The oligonucleotide composition as claimed in claim 1, wherein said composition comprises oligonucleotides SEQ ID NO:8 and SEQ ID NO:9.

8. The oligonucleotide composition as claimed in claim 1, wherein said composition comprises oligonucleotides SEQ ID NO:10 and SEQ ID NO:11 or oligonucleotides SEQ ID NO:11 and SEQ ID NO:12.

9. The oligonucleotide composition as claimed in claim 1, wherein said composition comprises oligonucleotide SEQ ID NO:14 or an inverse complement thereof.

10. The oligonucleotide composition as claimed in claim 1, wherein said composition comprises oligonucleotide SEQ ID NO:15 or an inverse complement thereof.

11. The oligonucleotide composition as claimed in claims 9–10, wherein said composition further comprises an oligonucleotide selected from the group consisting of SEQ ID NO:4, and SEQ ID:5, or an inverse complement thereof, and which is labelled with a detectable marker.

12. The oligonucleotide composition as claimed in claims 9–10, wherein said oligonucleotide is labelled with a marker, and said composition further comprises oligonucleotide SEQ ID NO:3 or an inverse complement thereof.

13. A method for detecting the presence of *Borrelia burgdorferi* (Bb) comprising the steps of:
(A) hybridizing a test DNA sample with a capture oligonucleotide consisting of the sequence of SEQ ID NO:3 or an inverse complement thereof to obtain captured DNA, and
(B) hybridizing the resulting captured DNA of step (A) with a labelled oligonucleotide probe consisting of the sequence of SEQ ID NO:4 or SEQ ID NO:5, or an inverse complement thereof, wherein the labelled oligonucleotide is labelled with a detectable marker, wherein detection of hybridization of the probe to said captured DNA is indicative of the presence of said *Borrelia burgdorferi* (Bb).

14. A method for detecting the presence of *Borrelia burgdorferi* (Bb) group I strain comprising the steps of:
(A) hybridizing a test DNA sample with a capture oligonucleotide consisting of the sequence of SEQ ID NO:13 or an inverse complement thereof to obtain captured DNA, and
(B) hybridizing the resulting captured DNA of step (A) with a labelled oligonucleotide probe consisting of the sequence of SEQ ID NO:4 or SEQ ID NO:5, or an inverse complement thereof, wherein the labelled oligonucleotide is labelled with a detectable marker, wherein detection of hybridization of the probe to said captured DNA is indicative of the presence of said *Borrelia burgdorferi* (Bb) group I strain.

15. The method as claimed in claim 14, wherein said strain is B31.

16. A method for detecting the presence of *Borrelia burgdorferi* (Bb) group II strain comprising the steps of:
(A) hybridizing a test DNA sample with a capture oligonucleotide consisting of the sequence of SEQ ID NO:14 or an inverse complement thereof to obtain captured DNA, and
(B) hybridizing the resulting captured DNA of step (A) with a labelled oligonucleotide probe consisting of the sequence of SEQ ID NO:4 or SEQ ID NO:5, or an inverse complement thereof, wherein the labelled oligonucleotide is labelled with a detectable marker, wherein detection of hybridization of the probe to said captured DNA is indicative of the presence of said *Borrelia burgdorferi* (Bb) group II strain.

17. The method as claimed in claim 16, wherein said strain is B29.

18. A method for detecting the presence of *Borrelia burgdorferi* (Bb) group III strain comprising the steps of:
(A) hybridizing a test DNA sample with a capture oligonucleotide consisting of the sequence of SEQ ID NO:15 or an inverse complement thereof to obtain captured DNA, and
(B) hybridizing the resulting captured DNA of step (A) with a labelled oligonucleotide probe consisting of the sequence of SEQ ID NO:4 or SEQ ID NO:5, or an inverse complement thereof, wherein the labelled oligonucleotide is labelled with a detectable marker, wherein detection of hybridization of the probe to said captured DNA is indicative of the presence of said *Borrelia burgdorferi* (b) group III strain.

19. The method as claimed in claim 18, wherein said strain is Aca1.

20. A method for detecting the presence of *Borrelia burgdorferi* (Bb) group I strain comprising the steps of:
(A) hybridizing a test DNA sample with a capture oligonucleotide consisting of the sequence of SEQ ID NO:3 or an inverse complement thereof to obtain captured DNA, and
(B) hybridizing the resulting captured DNA of step (A) with a labelled oligonucleotide probe consisting of the sequence of SEQ ID NO:13, or an inverse complement thereof, wherein the labelled oligonucleotide is labelled with a detectable marker, wherein detection of hybridization of the probe to said captured DNA is indicative of the presence of said *Borrelia burgdorferi* (Bb) group I strain.

21. The method as claimed in claim 20, wherein said strain is B31.

22. A method for detecting the presence of *Borrelia burgdorferi* (Bb) group II strain comprising the steps of:
(A) hybridizing a test DNA sample with a capture oligonucleotide consisting of the sequence of SEQ ID NO:3 or an inverse complement thereof to obtain captured DNA, and
(B) hybridizing the resulting captured DNA of step (A) with a labelled oligonucleotide probe consisting of the sequence of SEQ ID NO:14, or an inverse complement thereof, wherein the labelled oligonucleotide is labelled with a detectable marker, wherein detection of hybridization of the probe to said captured DNA is indicative of the presence of said *Borrelia burgdorferi* (Bb) group II strain.

23. The method as claimed in claim 22, wherein said strain is B29.

24. A method for detecting the presence of *Borrelia burgdorferi* (Bb) group III strain comprising the steps of:
(A) hybridizing a test DNA sample with a capture oligonucleotide consisting of the sequence of SEQ ID NO:3 or an inverse complement thereof to obtain captured DNA, and
(B) hybridizing the resulting captured DNA of step (A) with a labelled oligonucleotide probe consisting of the sequence of SEQ ID NO:15, or an inverse complement thereof, wherein the labelled oligonucleotide is labelled with a detectable marker, wherein detection of hybridization of the probe to said captured DNA is indicative of the presence of said *Borrelia burgdorferi* (Bb) group III strain.

25. The method as claimed in claim 24, wherein said strain is Aca1.

26. A method for amplifying *Borrelia burgdorferi* (Bb) DNA comprising the steps of:

(A) annealing a primer pair consisting of the sequence SEQ ID NO:1 and SEQ ID NO:2 to a Bb DNA sample; and (B) carrying out DNA amplification on the resulting product of step (A) so as to amplify said *Borrelia burgdorferi* (Bb) DNA.

27. A method for amplifying *Borrelia burgdorferi* (Bb) group I strain DNA comprising the steps of:

(A) annealing a primer pair consisting of the sequence of SEQ ID NO:6 and SEQ ID NO:7 to a Bb group I strain DNA sample; and (B) carrying out DNA amplification on the resulting product of step (A) so as to amplify said *Borrelia burgdorferi* (Bb) group I strain DNA.

28. The method as claimed in claim 27, wherein said strain is B31.

29. A method for amplifying *Borrelia burgdorferi* (Bb) group II strain DNA comprising the steps of:

(A) annealing a primer pair consisting of the sequence of SEQ ID NO:8 and SEQ ID NO:9 to a Bb group II strain DNA sample; and (B) carrying out DNA amplification on the resulting product of step (A) so as to amplify said *Borrelia burgdorferi* (Bb) group II strain DNA.

30. The method as claimed in claim 29, wherein said strain is B29.

31. A method for amplifying *Borrelia burgdorferi* (Bb) group III strain DNA comprising the steps of:

(A) annealing a primer pair consisting of the sequence of SEQ ID NO:10 and SEQ ID NO:11 or SEQ ID NO:11 and SEQ ID NO:12 to a Bb group III strain DNA sample; and (B) carrying out DNA amplification on the resulting product of step (A) so as to amplify said *Borrelia burgdorferi* (b) group III strain DNA.

32. The method as claimed in claim 31, wherein said strain is Aca1.

33. An oligonucleotide composition useful for detecting at least one strain of *Borrelia burgdorferi* (Bb) by molecular hybridization, comprising oligonucleotide SEQ ID NO:13, or an inverse complement thereof; and an oligonucleotide selected from the group consisting of SEQ ID NO:4, and SEQ ID:5, or an inverse complement thereof, and which is labelled with a detectable marker.

34. An oligonucleotide composition useful for detecting at least one strain of *Borrelia burgdorferi* (Bb) by molecular hybridization, comprising oligonucleotide SEQ ID NO:13, or an inverse complement thereof, and which is labelled with a detectable marker; and oligonucleotide SEQ ID NO:3, or an inverse complement thereof.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i i ) HYPOTHETICAL: NO ( v i ) ORIGINAL SOURCE: Outer Surface Protein A (OspA)
        ( A ) ORGANISM: *Borrelia burgdorferi*
        ( B ) STRAIN: B31
        ( G ) CELL TYPE: Bacteria ( x i ) SEQUENCE DESCRIPTION: SEQ ID NO:1:

AATAGGTCTA ATATTAGCCT TAATAGC              27

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i i ) HYPOTHETICAL: NO ( v i ) ORIGINAL SOURCE: Outer Surface Protein A (OspA)
        ( A ) ORGANISM: *Borrelia burgdorferi*
        ( B ) STRAIN: B31
        ( G ) CELL TYPE: Bacteria ( x i ) SEQUENCE DESCRIPTION: SEQ ID NO:2:

CTAGTGTTTT GCCATCTTCT TTGAAAA              27

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i i ) HYPOTHETICAL: NO ( v i ) ORIGINAL SOURCE: Outer Surface Protein A (OspA)
        ( A ) ORGANISM: *Borrelia burgdorferi*
        ( B ) STRAIN: B31
        ( G ) CELL TYPE: Bacteria ( x i ) SEQUENCE DESCRIPTION: SEQ ID NO:3:

ATGAAAAAAT ATTTATTGGG AATAGGTCTA ATATTAGCCT TAATAGCATG        50

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i i ) HYPOTHETICAL: NO ( v i ) ORIGINAL SOURCE: Outer Surface Protein A (OspA)
        ( A ) ORGANISM: *Borrelia burgdorferi*

(B) STRAIN: B31
(G) CELL TYPE: Bacteria (xi) SEQUENCE DESCRIPTION: SEQ ID NO:4:

GCAACAGTAG ACAAGCTTGA GCTTAAAGGA ACTTC 35

(2) INFORMATION FOR SEQ ID NO:5:

(i) SEQUENCE CHARACTERISTICS:
(A) LENGTH: 23 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*
(B) STRAIN: B31
(G) CELL TYPE: Bacteria (xi) SEQUENCE DESCRIPTION: SEQ ID NO:5:

TTTTCAAAGA AGATGGCAAA ACA 23

(2) INFORMATION FOR SEQ ID NO:6:

(i) SEQUENCE CHARACTERISTICS:
(A) LENGTH: 27 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*
(B) STRAIN: B31
(G) CELL TYPE: Bacteria (xi) SEQUENCE DESCRIPTION: SEQ ID NO:6:

AACAAAGACG GCAAGTACGA TCTAATT 27

(2) INFORMATION FOR SEQ ID NO:7:

(i) SEQUENCE CHARACTERISTICS:
(A) LENGTH: 28 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*
(B) STRAIN: B31
(G) CELL TYPE: Bacteria (xi) SEQUENCE DESCRIPTION: SEQ ID NO:7:

TTACAGTAAT TGTTAAAGTT GAAGTGCC 28

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*

(B) STRAIN: B29
(G) CELL TYPE: Bacteria (xi) SEQUENCE DESCRIPTION: SEQ ID NO:8:

TGATAAAAAC AACGGTTCTG GAAC 24

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*
(B) STRAIN: B29
(G) CELL TYPE: Bacteria (xi) SEQUENCE DESCRIPTION: SEQ ID NO:9:

GTAACTTTCA ATGTTGTTTT GCCG 24

(2) INFORMATION FOR SEQ ID NO:10:

(i) SEQUENCE CHARACTERISTICS:
(A) LENGTH: 27 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*
(B) STRAIN: AcaI
(G) CELL TYPE: Bacteria (xi) SEQUENCE DESCRIPTION: SEQ ID NO:10:

GAAAAAGGTG AATTGTCTGC AAAAACC 27

(2) INFORMATION FOR SEQ ID NO:11:

(i) SEQUENCE CHARACTERISTICS:
(A) LENGTH: 29 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*
(B) STRAIN: AcaI
(G) CELL TYPE: Bacteria (xi) SEQUENCE DESCRIPTION: SEQ ID NO:11:

TTCCAATGTT ACTTTATCAT TAGCTACTT 29

(2) INFORMATION FOR SEQ ID NO:12:

(i) SEQUENCE CHARACTERISTICS:
(A) LENGTH: 28 base pairs
(B) TYPE: nucleic acid
(C) STRANDEDNESS: single
(D) TOPOLOGY: linear (iii) HYPOTHETICAL: NO (vi) ORIGINAL SOURCE: Outer Surface Protein A (OspA)
(A) ORGANISM: *Borrelia burgdorferi*

(B) STRAIN: AcaI
        (G) CELL TYPE: Bacteria (xi) SEQUENCE DESCRIPTION: SEQ ID NO:12:

TAAAGACAAA ACATCAACAG ATGAAATG                                28

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (iii) HYPOTHETICAL: NO (vi) ORIGINAL SOURCE: Outer Surface Protein A (OspA)
        (A) ORGANISM: Borrelia burgdorferi
        (B) STRAIN: B31
        (G) CELL TYPE: Bacteria (xi) SEQUENCE DESCRIPTION: SEQ ID NO:13:

CTGCAGCTTG GAATTCAGGC ACT                                     23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (iii) HYPOTHETICAL: NO (vi) ORIGINAL SOURCE: Outer Surface Protein A (OspA)
        (A) ORGANISM: Borrelia burgdorferi
        (B) STRAIN: B29
        (G) CELL TYPE: Bacteria (xi) SEQUENCE DESCRIPTION: SEQ ID NO:14:

ACTCTAGCTG CTGACGGCAA AAC                                     23

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (iii) HYPOTHETICAL: NO (vi) ORIGINAL SOURCE: Outer Surface Protein A (OspA)
        (A) ORGANISM: Borrelia burgdorferi
        (B) STRAIN: AcaI
        (G) CELL TYPE: Bacteria (xi) SEQUENCE DESCRIPTION: SEQ ID NO:15:

AGGAAAAGTA GCTAATGATA AAGTAACA                                28